United States Patent [19]

Bauer et al.

[11] 4,212,650
[45] Jul. 15, 1980

[54] DIAGNOSTIC PROCESS

[75] Inventors: Hartwig W. Bauer, Heidenheim; Wolfgang Ax, Marburg an der Lahn, both of Fed. Rep. of Germany

[73] Assignee: Behringwerke Aktiengesellschaft, Marburg an der Lahn, Fed. Rep. of Germany

[21] Appl. No.: 959,011

[22] Filed: Nov. 9, 1978

[30] Foreign Application Priority Data

Nov. 11, 1977 [DE] Fed. Rep. of Germany ....... 2750521

[51] Int. Cl.² ...................... G01N 27/26; G01N 33/16
[52] U.S. Cl. .................................... 23/230 B; 23/912; 204/180 R
[58] Field of Search .............................. 23/230B, 912; 204/180 R

[56] References Cited

U.S. PATENT DOCUMENTS

| 4,043,757 | 8/1977 | Wagstaff | 23/230 B |
| 4,081,241 | 3/1978 | Porzsolt | 23/230 B |

FOREIGN PATENT DOCUMENTS 2659864 10/1977 Fed. Rep. of Germany ............. 23/912

*Primary Examiner*—Sidney Marantz
*Attorney, Agent, or Firm*—Curtis, Morris & Safford

[57] ABSTRACT

A process for an in vitro determination of the immunization status of cells of human beings and animals by measuring in an electric field the changed mobility of charged indicator particles which have been treated with a medium of lymphocytes incubated with a synthetic peptide of high basicity.

11 Claims, No Drawings

DIAGNOSTIC PROCESS

This invention relates to a process for an in vitro determination of the immunization status of cells of human beings and animals by measuring in an electric field the changed mobility of charged indicator particles which have been treated with a medium of lymphocytes incubated with antigens.

U.S. Pat. No. 4,081,241 describes a process for an in vitro determination in which lymphocytes are incubated with antigens, the incubation mixture or the cell-free supernatant is admixed with a dispersion of indicator particles and the mobility of the indicator particles is measured in an electric field. As indicator particles those particles are used that show a substantially uniform behavior in the electrical field and undergo interactions with the lymphocyte supernatant whereby the behavior of the particles in the electric field is modified in a measurable manner. In a preferred embodiment denatured erythrocytes are used as indicator particles. As denaturing agents tannin or/and sulfosalicylic acid are preferred. With this process, going back to E. J. Field and E. A. Caspary, The Lancet, 1970, pages 1337 to 1341, it is possible to detect malignant diseases when the so-called encephalitogenic factor (EF) or a basic protein from central nervous tissue is used as an antigen.

Antigenic substances of this type are not only little defined but also accessible only with difficulty. Their properties depend on the proces of their manufacture. With a view to the importance of the detection of sensibilized lymphocytes for the diagnosis of malignant diseases it is, therefore, desirable to replace the antigen by a defined chemical substance.

It has now been found that EF or the basic protein from central nervous tissue can be replaced by synthetic peptides.

It is, therefore, the object of the invention to provide a process for an in vitro determination which comprises incubating lymphocytes with a synthetic peptide of high basicity and measuring the migration speed of the incubated lymphocytes in the electric field. Consequently, the lymphocytes act as indicator particles the electrical properties of which are modified in a measurable manner after their incubation with a synthetic peptide. During the incubation the mixture consisting of lymphozytes and the peptide undergoes a modification in its composition, which can be determined by the change in the electric behavior of a second particulate indicator. For determination of the modified electric properties the measurement of the migration speed in the electric field is preferably used.

Preferred basic peptides to be used in the process of the invention are synthetic polypeptides essentially consisting of lysine, arginine and/or ornithine, especially poly-L-lysine, poly-L-arginine or poly-L-ornithine, as well as homogeneous or heterogeneous mixtures thereof. It proved particularly advantageous to use poly-L-lysine having a molecular weight in the range of from 750 to 100,000, preferably 750 to 5,000. Poly-L-lysine has the advantage of being available in the form of substantially stable salts, for example a hydrobromide or hydrochloride.

The indicator particles can be the lymphocytes themselves, the electric behavior of which is modified in a measurable manner after their incubation with a synthetic peptide of high basicity. The process of the invention can, however, be rendered more sensitive when, instead of measuring the behavior of the lymphocytes, the modifications occuring in the incubation mixture during incubation are transferred to other indicator particles and the modified behavior of the latter is determined. Other indicator particles of this type are preferably those which show a practically uniform behavior in an electric field and undergo interactions with the constituents of the incubation mixture of synthetic peptide and lymphocytes in such a way that the behavior of the particles is modified in the electric field in a measurable manner and the interactions of the particles can be observed directly or measured by means of a suitable apparatus. Especially useful indicator particles are human or animal erythrocytes that have been treated with a denaturing agent, for example with tannin and/or sulfosalicylic acid. Preferred indicator particles are tanned erythrocytes stabilized with sulfosalicylic acid by the process according to Becht, J. Immunol. 101, pages 18 to 22 (1968). Liposome-membrane particles are suitable as well.

The lymphocytes are isolated in known manner from peripheral blood rendered non-coagulable in the usual manner, for example by adding an anticoagulant substance such as heparin. The purified lymphocytes obtained in this manner can then be incubated with the synthetic basic polypeptides under the conditions of the aforesaid process. When the incubation mixture contains lymphocytes that are sensibilized with tumor-associated antigens, substances, possibly so-called lymphokines, are set free. The interaction of said substances with the indicator particles leads to a modification of the migration speed of the particles in the electric field, which modification is measurable.

When tanned erythrocytes or other indicator particles are admixed with an incubation medium of the cell-free lymphocyte supernatant, it is recommended to add 1 to 10 ml, preferably 3 ml, of the incubation medium to 0.1 to 1.0 ml of a suspension containing $1 \times 10^7$ to $5 \times 10^7$ particles per ml.

The incubation medium can be prepared as follows: $1 \times 10^6$ to $1 \times 10^7$ lymphocytes from a test person, obtained by gradient centrifugation, are incubated with 0.01 to 100 µg of a synthetic peptide, preferably polylysine, for 90 to 1,800 minutes at 25° to 37° C. The lymphocytes are then separated from the supernatant, preferably by centrifugation, and the supernatant is admixed with the indicator particles as described above. It is not necessary to use the cell-free supernatant. The presence of lymphocytes has no detrimental effect.

The treated indicator particles are then analyzed, for example in a cell electrophoresis system in which the migration speed can be recorded. Evaluation is made by determining the deviation of the electrophoretic migration speed from the zero value and the value obtained with lymphocytes of healthy control persons. In the incubation supernatant lymphocyte of a patient suspected to have a tumor slow down the electrophoretic mobility of the indicator particles charged therewith as compared to indicator particles that have been obtained with a physiologically acceptable incubation medium (zero value) and to indicator particles obtained with the supernatant from the incubation of the polypeptide with lymphocyte of healthy persons. In diagnosis such a retardation is considered pathological.

The following example illustrates the invention.

EXAMPLE 25 ml of venous blood were taken from a test person with a syringe containing 0.5 ml of heparin. The blood sample was fed into a column (diameter 2 cm, height 30 cm) filled with glass beads (2 mm in diameter) and left to stand in an incubator for 90 minutes at 37° C. The eluate from the column was then diluted in a ratio of 1:4 with Hank's solution containing 0.05% of the $Na_2$ salt of ethylene-diamine tetracetic acid (EDTA). The dilute eluate was added to ¼ of its volume of a solution consisting of sodium, calcium, magnesium and methyl-glucamine salts of metrizoic acid (Ronpacon(R) by Cilag-Chemie, GmbH, Alsbach, Fed.Rep. of Germany) and a high molecular weight copolymer of saccharose and epichlorohydrin (Ficoll(R) by Pharmacia, Uppsala, Sweden) having a density of 1.074 and the whole was centrifuged for 15 minutes at 250 g. The lymphocyte ring superposing the density gradient was siphoned off and washed once with the aforesaid EDTA containing Hank's solution and then twice with Hank's solution. The cells were separated by centrifugation and taken up in 0.5 ml of RPMI 1640 medium without serum. RPMI 1640 medium is a culture medium for the growth of cells and consists of a mixture of amino acids, vitamins, inorganic salts, buffer substances and antibiotics in the following composition:

| Component | mg/l |
| --- | --- |
| $Ca(NO_3)_2 \cdot 4H_2O$ | 100.0 |
| KCl | 400.0 |
| $MgSO_4 \cdot 7H_2O$ | 100.0 |
| NaCl | 6000.0 |
| $NaHCO_3$ | 2000.0 |
| $Na_2HPO_4 \cdot 7H_2O$ | 1512.0 |
| glucose | 2000.0 |
| glutathione (reduced) | 1.0 |
| phenol-red | 5.0 |
| L-arginine (free base) | 200.0 |
| L-asparagine | 50.0 |
| L-aspartic acid | 20.0 |
| L-cystine | 50.0 |
| L-glutamic acid | 20.0 |
| L-glutamine | 300.0 |
| glycine | 10.0 |
| L-histidine (free base) | 15.0 |
| L-hydroxyproline | 20.0 |
| L-isoleucine (free from allo isomer) | 50.0 |
| L-leucine (free from methionine) | 50.0 |
| L-lysine HCl | 40.0 |
| L-methionine | 15.0 |
| L-phenylalanine | 15.0 |
| L-proline (free from hydroxyl-L-proline) | 20.0 |
| L-serine | 30.0 |
| L-threonine (free from allo isomer) | 20.0 |
| L-tryptophane | 5.0 |
| L-thyrosine | 20.0 |
| L-valine | 20.0 |
| biotine | 0.2 |
| D-Ca-pantothenate | 0.25 |
| cholin-chloride | 3.0 |
| folic acid | 1.0 |
| i-inosite | 35.0 |
| nicotine amide | 1.0 |
| para-aminobenzoic acid | 1.0 |
| pyridoxine HCl | 1.0 |
| riboflavine | 0.2 |
| thiamine HCl | 1.0 |
| vitamin $B_{12}$ | 0.005 |

RPMI 1640 medium has been described by G. E. Moore, A. A. Sandberg and K. Ulrich in J.Vat.Can.Inst., 36/3; 405 (March, 1966) and is available on the market.

The number of cells was determined in a Coulter Counter (manufacturer: Coulter Electronics, Krefeld, Fed.Rep. of Germany) and the lymphocyte suspension was standardized with RPMI 1640 medium to $1 \times 10^7$ cells per ml. 0.7 ml of the cell suspension was centrifuged and the sediment taken up in 3 ml of RPMI 1640 medium containing 0.01 mg/ml of poly-L-lysine having a molecular weight of 3,400 and the mixture was incubated for 18 hours. The lymphocytes were then separated by centrifugation and 3 ml of the supernatant were incubated for 1 to 2 hours with 1 ml of a cell suspension ($5 \times 10^7$ stabilized and tanned erythrocytes per ml of Hank's solution). For measuring, the cell suspension obtained was filled into an apparatus for cell electrophoresis and the electrophoretic migration of the particles was evaluated diagnostically for the presence of a cancerous disease.

As an apparatus for cell electrophoresis, a microscope was used which is suitable for determining the electric surface charge of suspended microscopic particles on the basis of their migration speed in the electric field (electrophoresis). The suspension used is contained in the measuring chamber of a so-called electrophoresis system. The optical axis of the microscope is arranged in horizontal position since the measuring chamber must be in a vertical position. In this manner influences, possibly affecting the measurement of the migration speed, are excluded.

What is claimed is:

1. An in vitro diagnostic method, which comprises incubating lymphocytes with a synthetic peptide of high basicity whereby the behavior of the lymphocytes in an electric field is modified in a detectable manner, subjecting the incubation mixture to an electric field, and measuring the migration speed of the lymphocytes in the electric field.

2. An in vitro diagnostic method, which comprises incubating lymphocytes with a synthetic peptide of high basicity whereby the behavior of the lymphocytes in an electric field is modified in a detectable manner, combining the incubation mixture with a dispersion of indicator particles, said particles exhibiting a substantially uniform behavior in an electric field and being interactive with said incubation mixture whereby their behavior in the electric field is modified in a detectable manner, and measuring the migration speed of the particles in the electric field.

3. An in vitro diagnostic method, which comprises incubating lymphocytes with a synthetic peptide of high basicity whereby the behavior of the lymphocytes in an electric field is modified in a detectable manner, separating the lymphocytes from the incubation mixture, combining the lymphocyte-free supernatant of the incubation mixture with a dispersion of indicator particles, said particles exhibiting a substantially uniform behavior in an electric field and being interactive with said supernatant whereby their behavior in the electric field is modified in a detectable manner, and measuring the migration speed of the particles in the electric field.

4. A method as claimed in claim 1, 2 or 3, wherein the synthetic peptide of high basicity is a synthetic polypeptide consisting essentially of lysine, arginine, ornithine, or a mixture thereof.

5. A method as defined in claim 4 wherein the synthetic polypeptide consists essentially of poly-L-lysine, poly-L-arginine, poly-L-ornithine, or a heterogeneous or homogeneous mixture thereof.

6. A method as defined in claim 5, wherein the synthetic peptide of high basicity is poly-L-lysine of a molecular weight in the range of from 750 to 100,000.

7. A method as defined in claim 6, wherein the synthetic peptide is of a molecular weight in the range of from 750 to 5,000.

8. A method as defined in claim 2 or 3, wherein the indicator particles are denatured human or animal erythrocytes.

9. A method as defined in claim 8, wherein the indicator particles are tanned erythrocytes stabilized with sulfosalicylic acid.

10. A method as defined in claim 3, wherein the supernatant is added to the dispersion of indicator particles in the proportion of from 1 to 10 ml of supernatant to from 0.1 to 1.0 ml of said dispersion containing from $1 \times 10^7$ to $5 \times 10^7$ particles per milliliter.

11. A method as defined in claim 2 or 3 wherein the indicator particles are liposome-membrane particles.

* * * * *